(12) United States Patent
Kim et al.

(10) Patent No.: US 11,141,407 B2
(45) Date of Patent: Oct. 12, 2021

(54) PHARMACEUTICAL COMPOSITION FOR PREVENTING OR TREATING AIDS COMPRISING RHODANINE DERIVATIVE

(71) Applicant: AVIXGEN INC., Seoul (KR)

(72) Inventors: Min Jung Kim, Seoul (KR); Jun Sub Choi, Yongin-si (KR); Hye Cheong Koo, Gwangmyeong-si (KR); Yi Yong Baek, Goyang-si (KR)

(73) Assignee: AVIXGEN INC., Seoul (KR)

( * ) Notice: Subject to any disclaimer, the term of this patent is extended or adjusted under 35 U.S.C. 154(b) by 0 days.

(21) Appl. No.: 17/024,255

(22) Filed: Sep. 17, 2020

(65) Prior Publication Data

US 2021/0000802 A1   Jan. 7, 2021

Related U.S. Application Data

(60) Division of application No. 16/555,998, filed on Aug. 29, 2019, now Pat. No. 10,821,101, which is a continuation of application No. PCT/KR2019/004855, filed on Apr. 23, 2019.

(30) Foreign Application Priority Data

May 16, 2018   (KR) .................. 10-2018-0056007

(51) Int. Cl.
| | | |
|---|---|---|
| A61K 31/427 | (2006.01) | |
| A61P 31/18 | (2006.01) | |
| A61K 31/52 | (2006.01) | |
| A61K 31/675 | (2006.01) | |
| A61K 31/7068 | (2006.01) | |
| A61K 31/7076 | (2006.01) | |

(52) U.S. Cl.
CPC ............ *A61K 31/427* (2013.01); *A61P 31/18* (2018.01); *A61K 31/52* (2013.01); *A61K 31/675* (2013.01); *A61K 31/7068* (2013.01); *A61K 31/7076* (2013.01)

(58) Field of Classification Search
CPC combination set(s) only.
See application file for complete search history.

(56) References Cited

U.S. PATENT DOCUMENTS 7,625,917 B2 * 12/2009 Turpin ................. C07D 213/04
424/204.1

FOREIGN PATENT DOCUMENTS

| JP | 2003-252794 A | 9/2003 |
|---|---|---|
| JP | 2011-502998 A | 1/2011 |
| KR | 10-2006-0026402 A | 3/2006 |
| KR | 10-2007-0114806 A | 12/2007 |
| KR | 10-2011-0137939 A | 12/2011 |
| KR | 10-1893988 A | 8/2018 |
| WO | 00/10573 A1 | 3/2000 |

OTHER PUBLICATIONS

Tallarida, "Quantitative Methods for Assessing Drug Synergism," Genes Cancer. Nov. 2011; 2(11): 1003-1008.*
Kim et al., "Identification and characterization of a new type of inhibitor against the human immunodeficiency virus type-1 nucleocapsid protein", Retrovirology, vol. 12, No. 90—16 pages (2015).
International Search Report of corresponding PCT Application No. PCT/KR2019/004855—8 pages (dated Aug. 5, 2019).
Written Opinion of corresponding PCT Application No. PCT/KR2019/004855—6 pages (dated Aug. 5, 2019).

* cited by examiner

*Primary Examiner* — Jared Barsky
(74) *Attorney, Agent, or Firm* — Sughrue Mion, PLLC

(57) ABSTRACT

The present invention relates to a pharmaceutical composition for preventing or treating AIDS, comprising a rhodanine derivative and a nucleoside reverse transcriptase inhibitor. A complex composition of the present invention exhibits a synergistic effect in terms of anti-HIV activity as compared with a case where each of the compounds is used as a single drug. Thus, the composition provides sufficient anti-HIV activity and exhibits an excellent effect of decreasing side effects such as toxicity even in a case where each compound is administered in a small amount. Accordingly, the present invention is expected to greatly contribute to treatment of AIDS patients.

3 Claims, 13 Drawing Sheets

[FIG. 1]
(A)
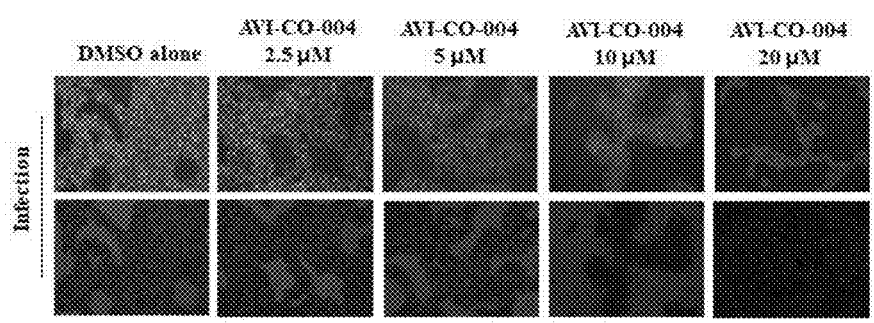
(B)
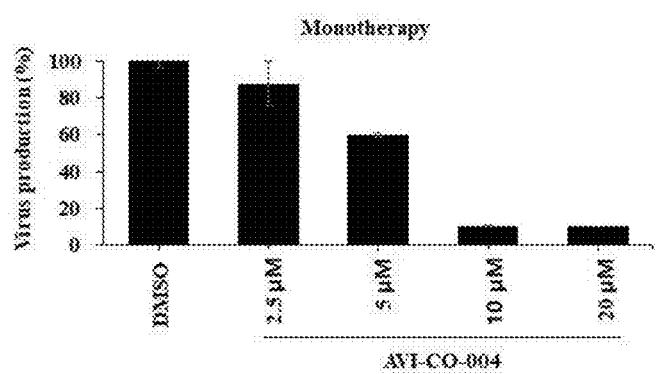

[FIG. 2]
(A)
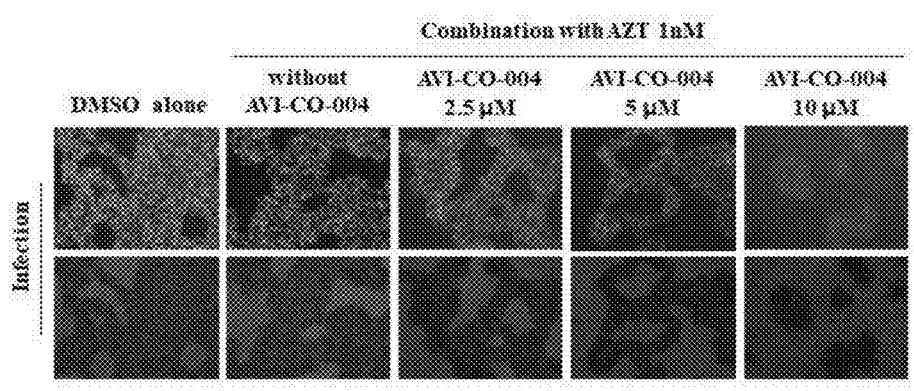
(B)
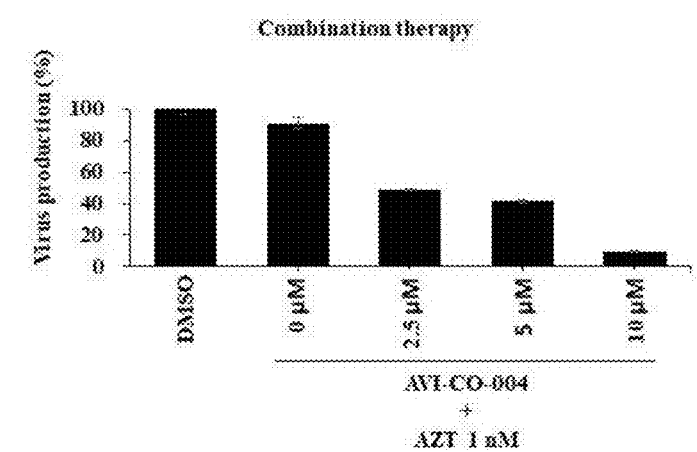

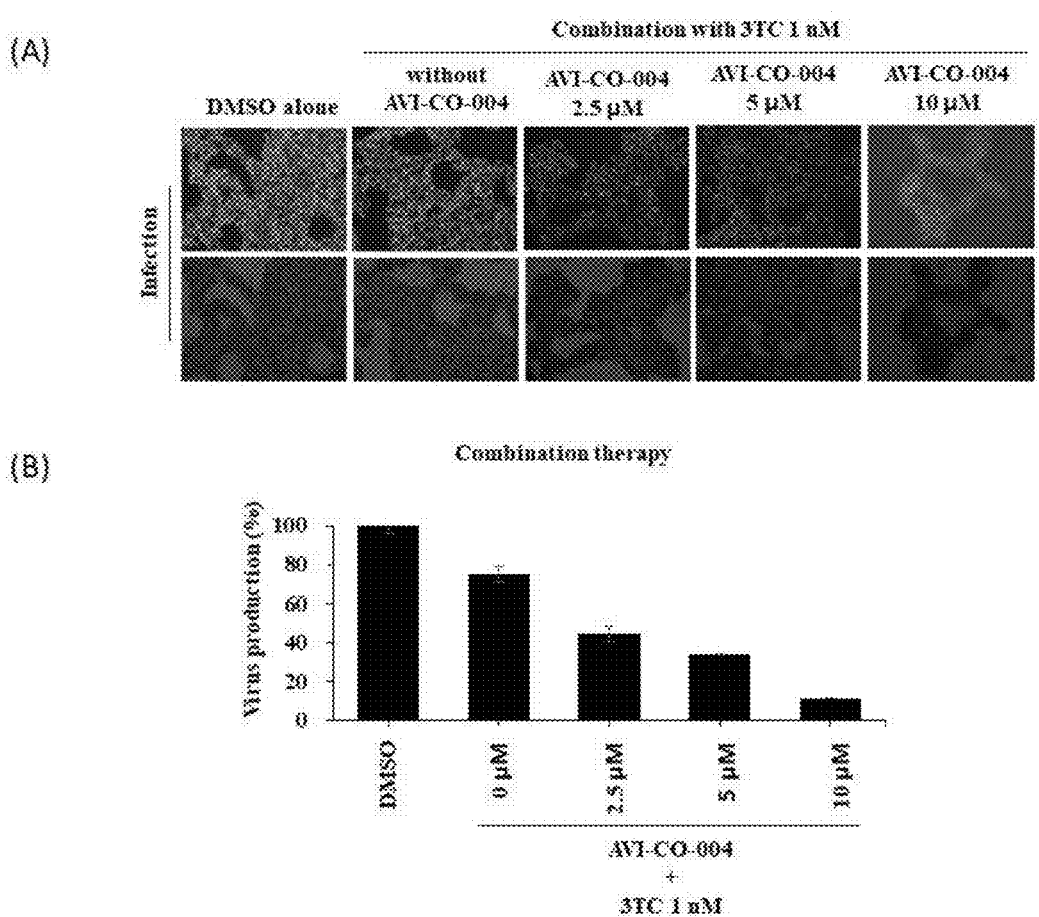
[FIG. 3]

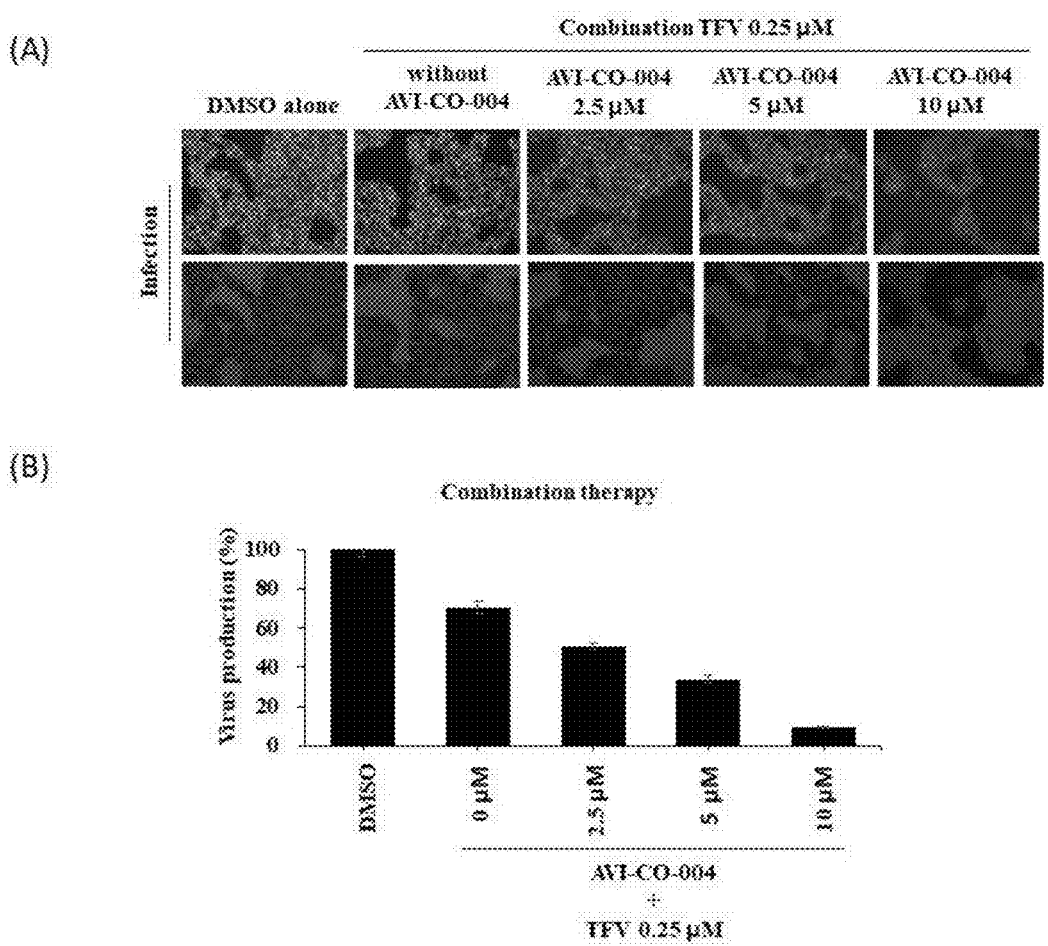

[FIG. 5]
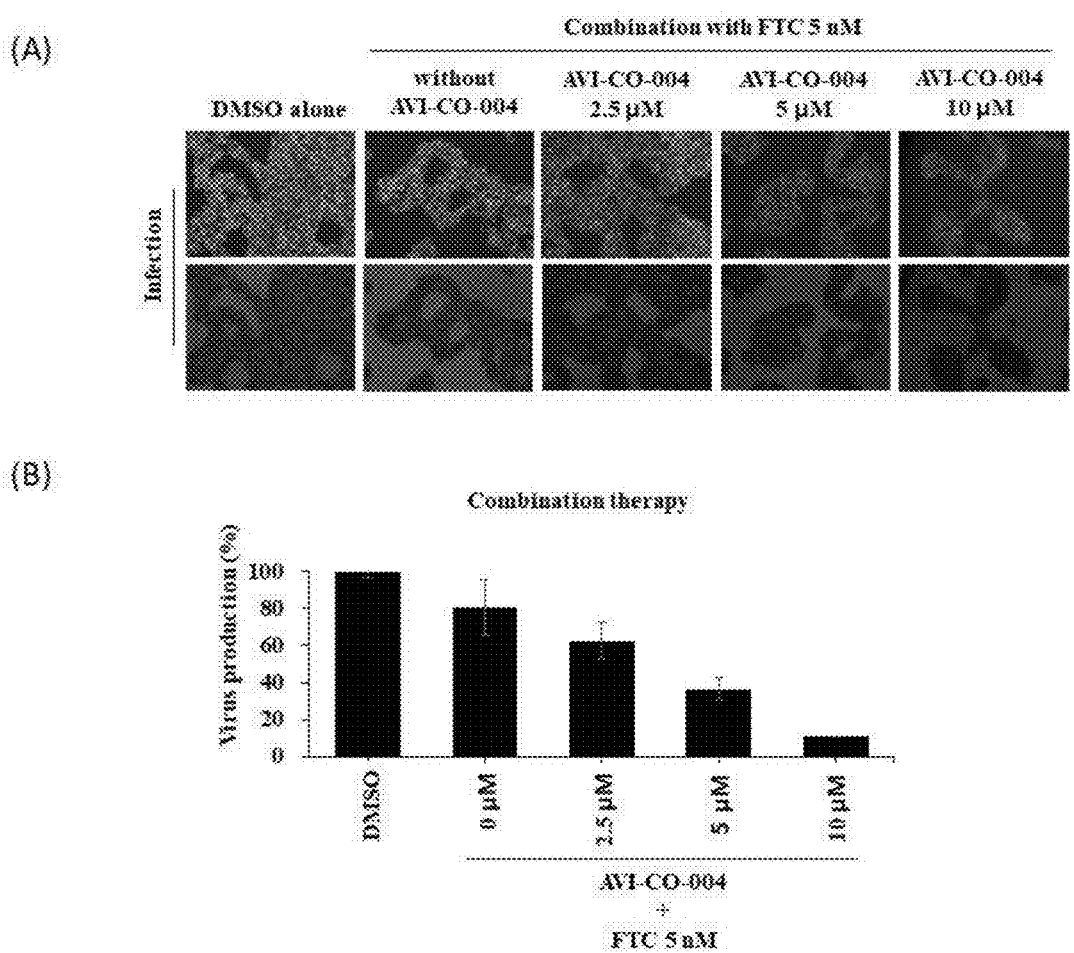

[FIG. 6]
A
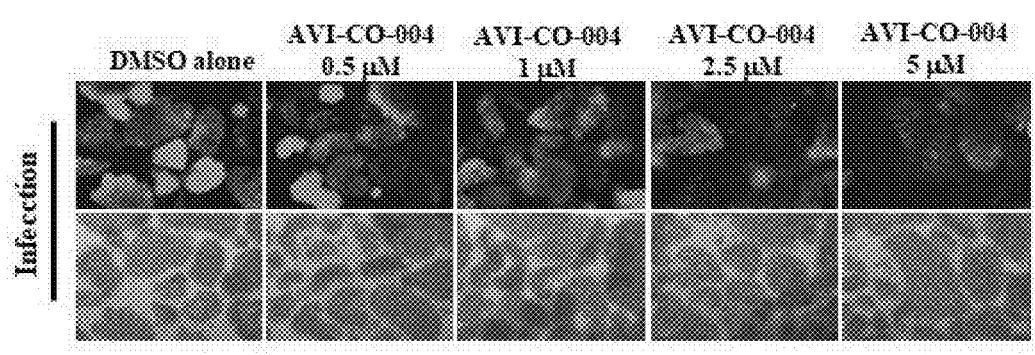
B
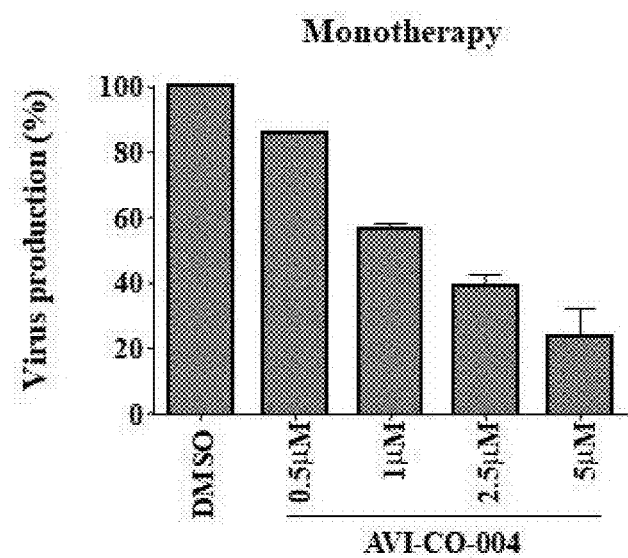

[FIG. 7]
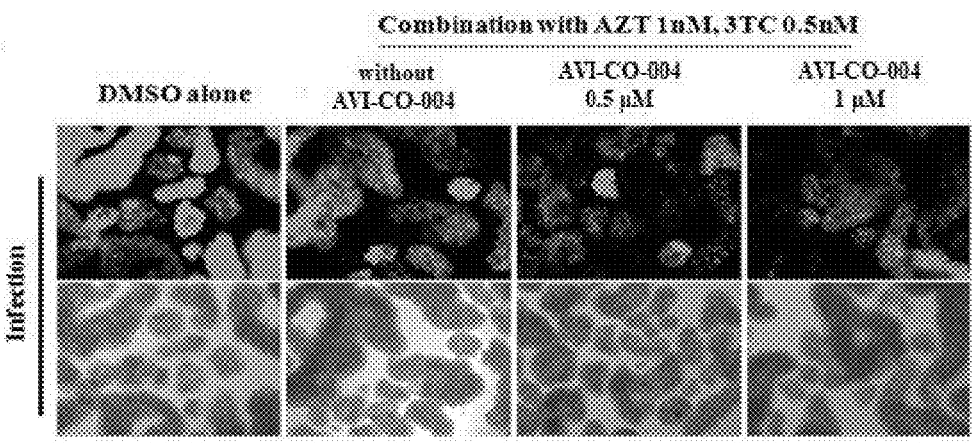
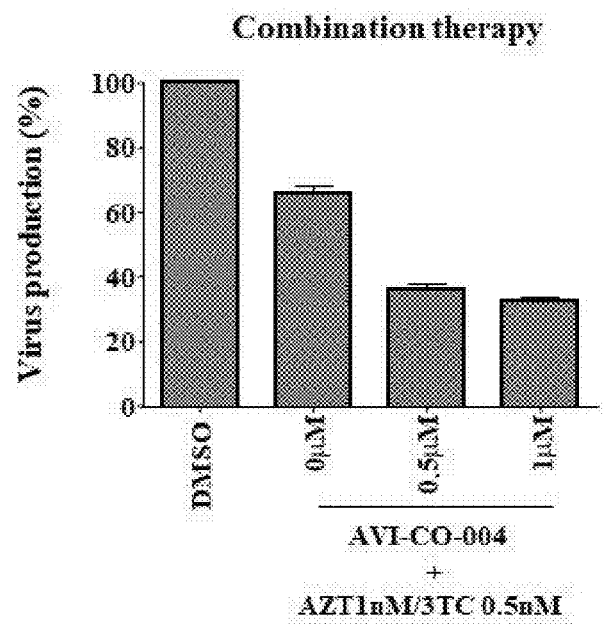

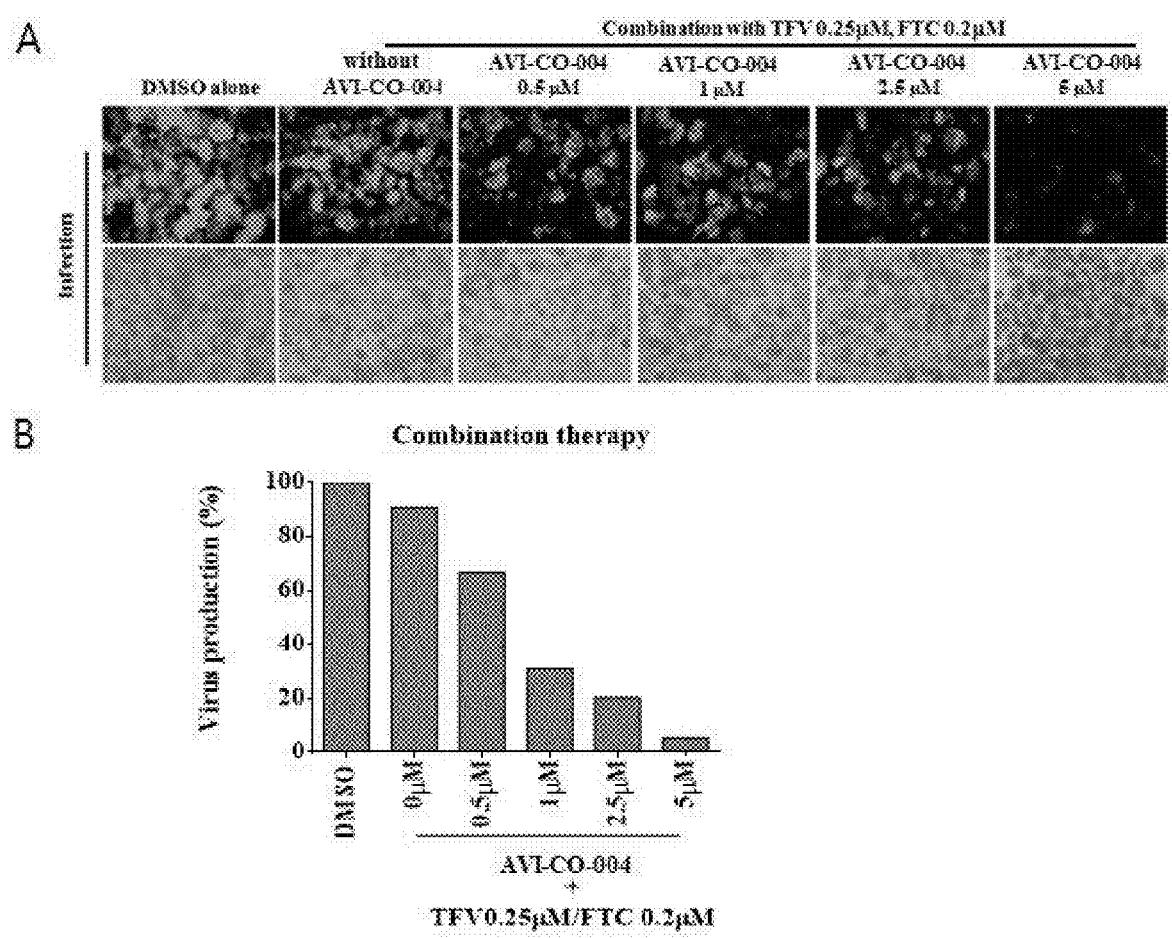
[FIG. 8]

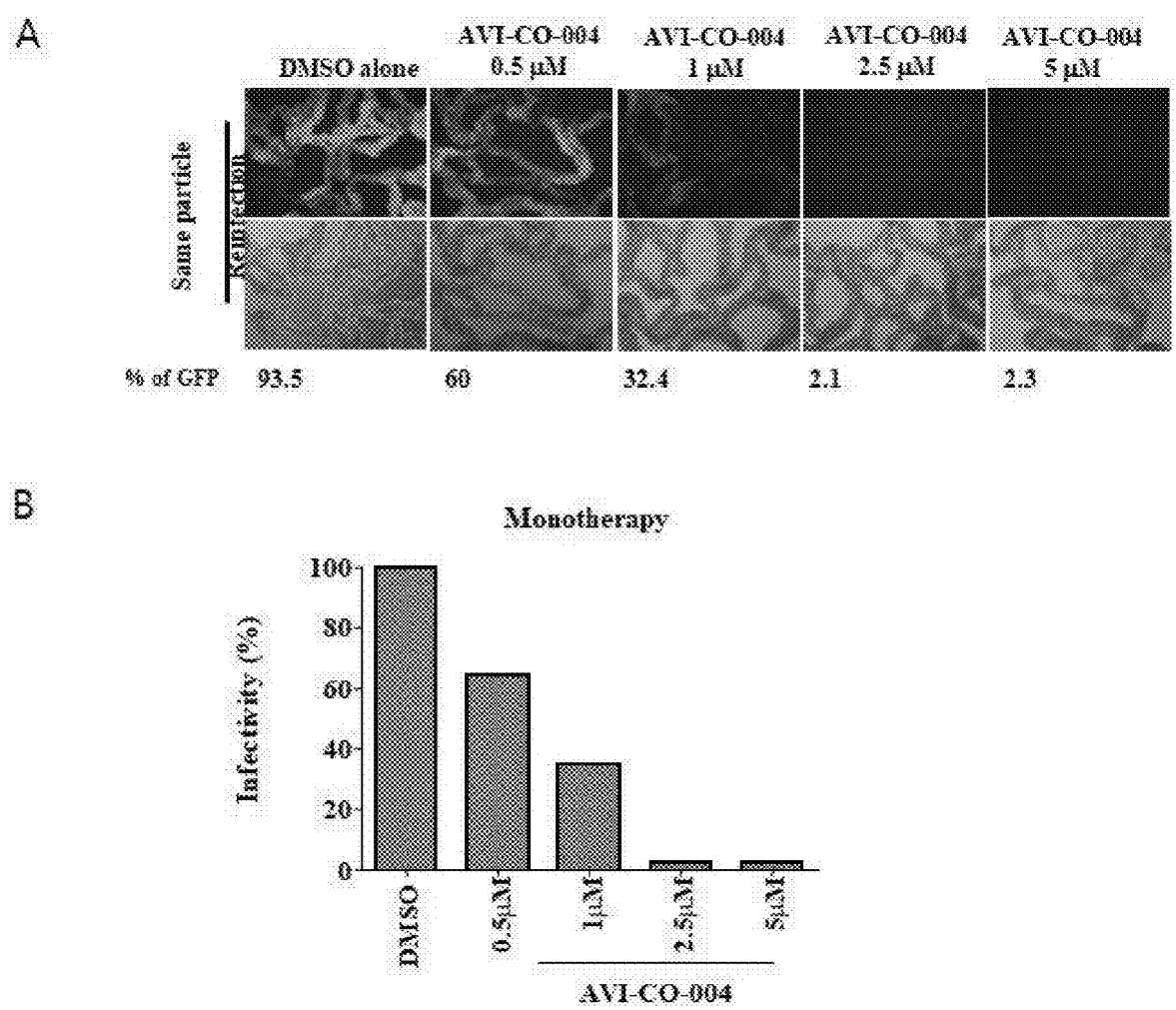
[FIG. 9]

[FIG. 10]
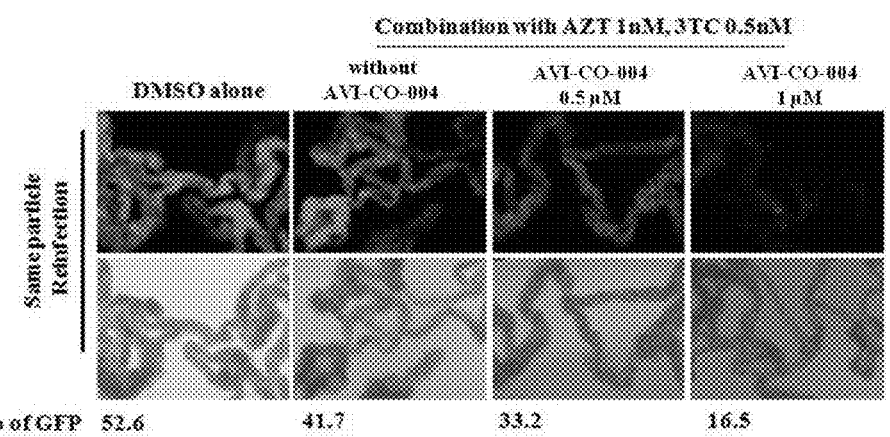
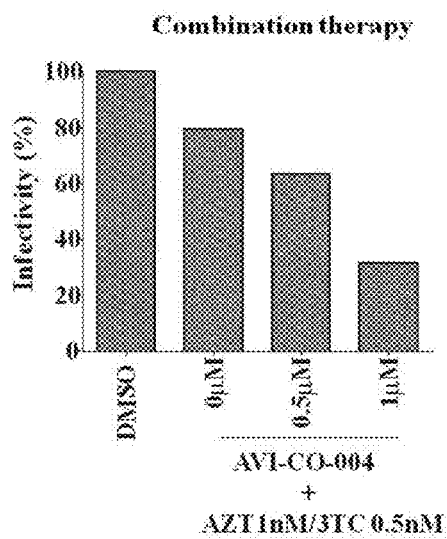

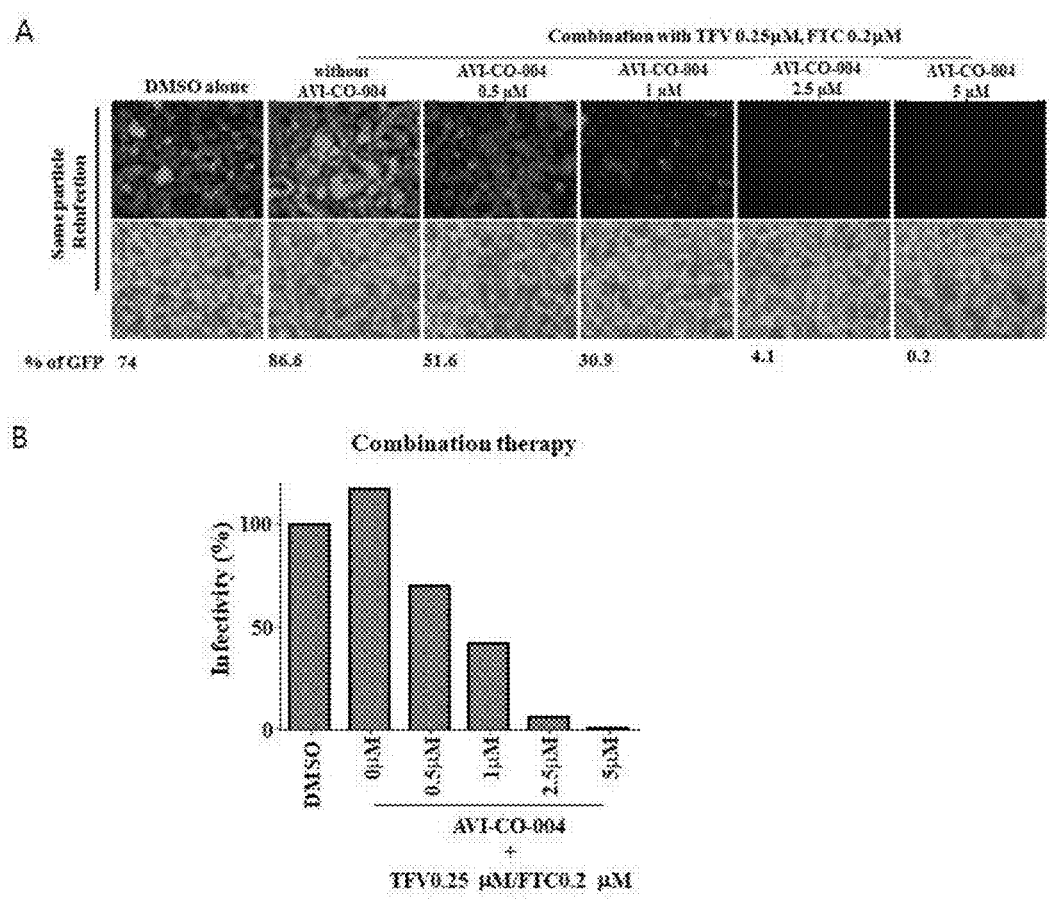
[FIG. 11]

[FIG. 12]
A
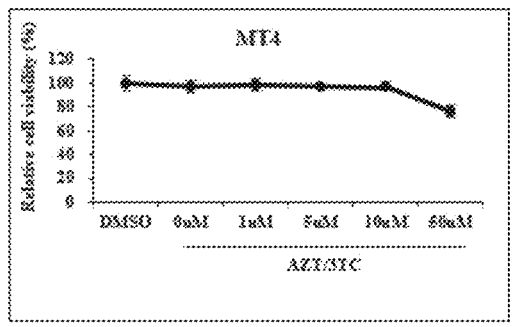
B
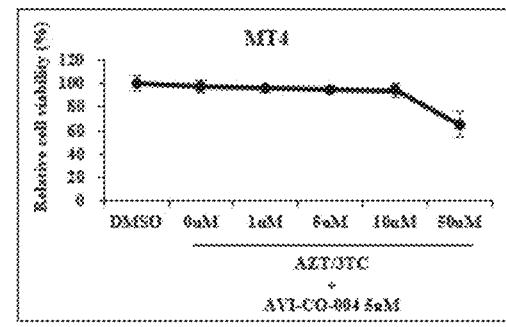
C
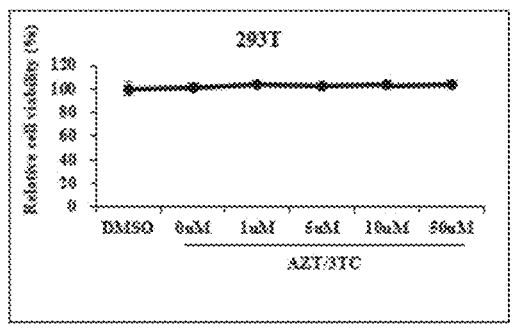
D
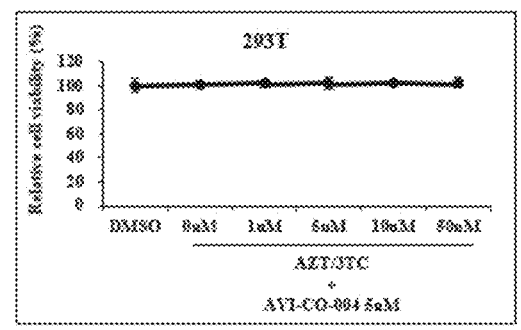

[FIG. 13]
A
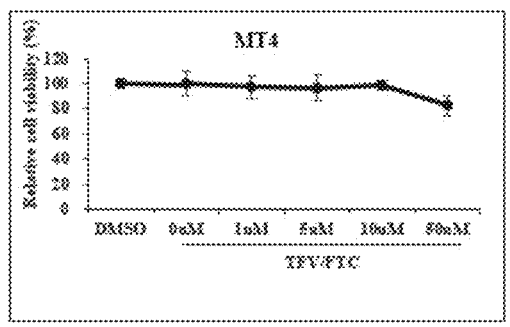
B
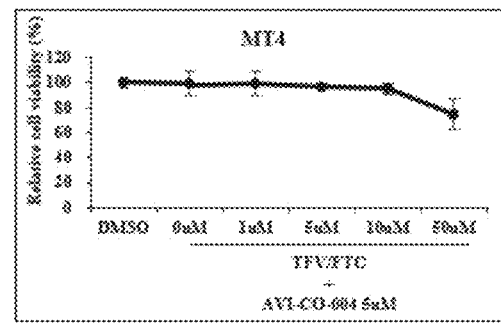
C
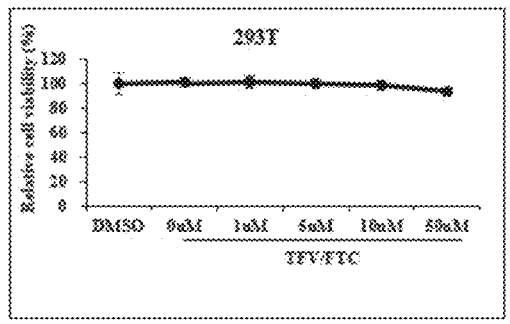
D
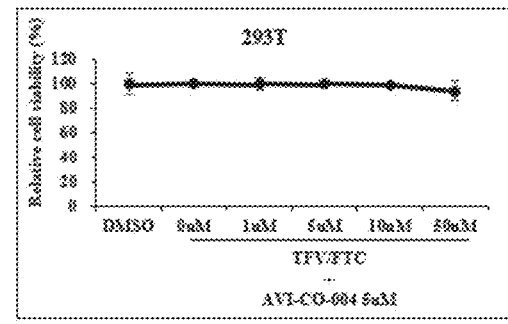

PHARMACEUTICAL COMPOSITION FOR PREVENTING OR TREATING AIDS COMPRISING RHODANINE DERIVATIVE

CROSS-REFERENCE TO RELATED APPLICATIONS

This application is a Divisional Application of U.S. application Ser. No. 16/555,998, filed Aug. 29, 2019, which is a Continuation of International Application No. PCT/KR2019/004855 filed Apr. 23, 2019, claiming priority to Korean Patent Application No. 10-2018-0056007, filed May 16, 2018, the disclosures of which are incorporated herein by reference in their respective entireties.

TECHNICAL FIELD

The present invention relates to preventing or treating AIDS.

BACKGROUND ART

Acquired immune deficiency syndrome (AIDS) is an incurable disease caused by human immunodeficiency virus (HIV), and is prevalent all over the world. Research and development of therapeutic agents therefor are also carried out on a global scale, and no satisfactory results have been achieved yet. Currently, for anti-HIV compounds that have been clinically used or tested, nucleic acid-based derivatives such as 3'-azido-3'-deoxythymidine (AZT), 2',3'-di-deoxyinosine (ddI), dideoxycytidine (ddC), T-3'-didehydro-3'-deoxythymidine (d4T), and 2'-3'-dideoxy-3'-thiacyti(3TC) are exemplified as main therapeutic agents.

Clinical use shows that the above-mentioned drugs have many problems including 1) cytotoxicity; 2) emergence of mutated viruses which are drug-resistant, caused by long-term administration thereof, and thus decreased drug efficacy; 3) severe side effects such as pancreatitis, anemia, leukopenia, neutropenia, vomiting, dysphagia, gastric disorder, rash, insomnia, confusion, muscle cramps, dyspnea, dysuria, and hearing impairment; and the like.

In order to solve the problems, attempts have been made several times to devise a combined therapy to date. For example, a combination of a 150 mg dose of lamivudine (which is a nucleoside RT inhibitor or is also called 3TC) and a 300 mg dose of zidovudine (which is a nucleotide RT inhibitor or is also called AZT) is formulated into an oral tablet and administered twice a day; or a combination of a 600 mg dose of abacavir (which is a nucleoside RT inhibitor), a 150 mg dose of lamivudine, and a 300 mg dose of zidovudine is formulated into an oral tablet and administered twice a day.

Despite current combination therapies, problems such as severe side effects of anti-HIV compounds and emergence of resistant viruses are still pointed out. Accordingly, there is a need for potent therapies against wild-type HIV viruses and resistant HIV viruses, and there is still a demand for novel combinations of anti-HIV compounds which restrict or inhibit recurrence of drug-resistant viruses, can be used for a long period of time, have long-lasting efficacy, and have a low pill burden.

In previous studies, while studying AIDS therapeutic agents with few side effects and less emergence of resistant viruses, the present inventors prepared novel rhodanine derivatives and identified that the rhodanine derivatives have excellent HIV inhibitory activity (Korean Patent No. 10-1159000). Subsequently, through continuous studies, the present inventors have found that when 3-{5-[5-(4-chlorophenyl)-furan-2-ylmethylene]-4-oxo-2-thioxo-thiazolidin-3-yl}-propionic acid (referred to as AVI-CO-004), which is one of the rhodanine derivatives, is used in combination with a specific type of anti-HIV compound, unique antiviral efficacy thereof is not inhibited while, at the same time, anti-HIV activity thereof is synergistically induced. Based on this finding, the present inventors have completed the present invention.

Technical Problem

Accordingly, an object of the present invention is to provide a combination of one or more therapeutically effective anti-HIV agents, thereby providing a combination of antiviral drugs which can have a complementary antiviral effect and a side effect-decreasing effect, can have a high level of barrier to resistance, and can be taken over a long period of time.

Another object of the present invention is to provide a method for treating or preventing AIDS, comprising a step of administering AVI-CO-004 or a pharmaceutically acceptable salt thereof, simultaneously or sequentially with one or more anti-HIV compounds.

Solution to Problem

In order to achieve the above-mentioned objects, the present invention provides a pharmaceutical composition for preventing or treating AIDS, comprising a compound represented by the following Formula 1 or a pharmaceutically acceptable salt thereof; and a nucleoside reverse transcriptase inhibitor.

[Formula 1]

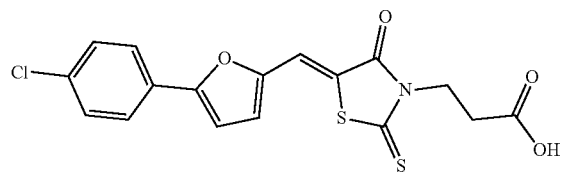

In addition, the present invention provides a method for treating or preventing AIDS, comprising a step of administering the compound represented by Formula (1) as described above or a pharmaceutically acceptable salt thereof, simultaneously or sequentially with one or more nucleoside reverse transcriptase inhibitors.

In addition, the present invention provides a use of a composition for the prevention or treatment of AIDS, the composition comprising the compound represented by Formula (1) as described above or a pharmaceutically acceptable salt thereof; and a nucleoside reverse transcriptase inhibitor.

Hereinafter, the present invention will be described in detail.

The present invention provides a pharmaceutical composition for preventing or treating acquired immune deficiency syndrome (AIDS), comprising, as active ingredients, 3-{5 [5-(4-chloro-phenyl)-furan-2-ylmethylene]-4-oxo-2-thioxo-thiazolidin-3-yl}-propionic acid (hereinafter referred to as AVI-CO-004) represented by the following Formula 1 and a nucleoside reverse transcriptase inhibitor.

[Formula 1]

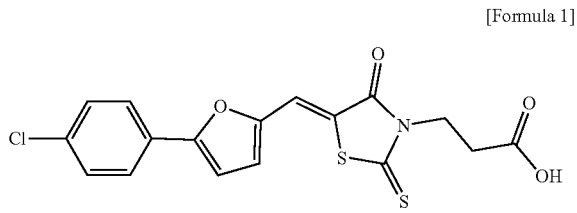 [SMILES: O=C(O)CCN1C(=O)/C(=C/c2ccc(-c3ccc(Cl)cc3)o2)SC1=S]

The AVI-CO-004 compound of the present invention is one of rhodanine derivatives and can be prepared as described in Korean Patent No. 10-1159000. AVI-CO-004 may be used in a base form or may be preferably used in the form of a suitable pharmaceutically acceptable salt; and the pharmaceutically acceptable salt includes a salt with an acidic or basic group which may exist in the rhodanine derivative unless specifically stated. The AVI-CO-004 compound can have not only anti-HIV activity, but also can cause non-infectious HIVs to be produced after treatment with the compound, thereby significantly decreasing viral proliferation (FIGS. 1 and 9).

As used herein, the term "compound exhibiting anti-HIV activity" means any compound having anti-HIV activity without particular limitation, and examples thereof include a nucleoside reverse transcriptase inhibitor, a non-nucleoside reverse transcriptase inhibitor, a protease inhibitor, a DNA polymerase inhibitor, a fusion inhibitor, an integrase inhibitor, a maturation inhibitor, and the like.

The pharmaceutical composition for preventing or treating AIDS according to the present invention comprises, as active ingredients, the AVI-CO-004 and one or more compounds exhibiting anti-HIV activity, and therefore, exhibits a synergistic effect in terms of anti-HIV activity as compared with a case where each of the compounds or the like is used as a single drug. Thus, the pharmaceutical composition provides sufficient anti-HIV activity and exhibits decreased side effects such as toxicity even in a case where each compound is administered in a smaller amount than a single drug thereof.

In an embodiment of the present invention, the compound exhibiting anti-HIV activity may be a nucleoside reverse transcriptase inhibitor (NRTI). The nucleoside reverse transcriptase inhibitor (NRTI) exhibits an anti-HIV effect by inhibiting a function of the reverse transcriptase of HIV, and examples thereof include zidovudine (3'-azido-3'-deoxythymidine, AZT), didanosine (2',3'-di-deoxyinosine, ddI), lamivudine (2'-3'-dideoxy-3'-thiacytidine, 3TC), stavudine (2'-3'-didehydro-3'-deoxythymidine, d4T), abacavir (ABC), emtricitabine (cis-4-amino-5-fluoro-1-[2-hydroxymethyl]-1,3-oxathiolan-5-yl]-2(1H)-pyrimidinone, FTC), and tenofovir disoproxil fumarate (TDF).

In the present invention, among compounds exhibiting anti-HIV activity, the nucleoside reverse transcriptase inhibitor is preferable from the viewpoint of synergistically inducing an antiviral effect without decreasing non-infectious virus-producing efficacy of AVI-CO-004.

To date, it has not been known that a mixture of 3-{5[5-(4-chloro-phenyl)-furan-2-ylmethylene]-4-oxo-2-thioxothiazolidin-3-yl}-propionic acid referred to as AVI-CO-004 and a nucleoside reverse transcriptase inhibitor exhibits a synergistic effect in terms of non-infectious virus-producing efficacy and antiviral efficacy.

In an embodiment of the present invention, the nucleoside reverse transcriptase inhibitor may be a combination of zidovudine (AZT) and lamivudine (3TC).

In an embodiment of the present invention, the nucleoside reverse transcriptase inhibitor may consist of emtricitabine (FTC) and tenofovir (TFV), or may consist of emtricitabine (FTC) and tenofovir disoproxil fumarate (TDF) which is a prodrug of tenofovir.

In a case where AZT is used at an early stage of infection, AZT ameliorates a clinical condition to a certain extent. However, AZT has limitations as an AIDS therapeutic agent from the viewpoints that AZT does not have an effect on prolonging the patient's life, has side effects such as exhibiting toxicity to the bone marrow, causes emergence of resistant viruses in a case of being used for a long period of time, and the like. Although less toxic than AZT, 3TC, FTC, TFV, and the like also cause resistant viruses to be produced, or have low antiviral efficacy. Taking these into consideration, a decrease in amount used due to a synergistic effect can be achieved by using a minimal amount of a nucleoside reverse transcriptase inhibitor to ensure safety and inhibit production of resistant viruses, in which the nucleoside reverse transcriptase inhibitor is used as a mixture with AVI-CO-004 having superior antiviral efficacy.

In a preferred embodiment of the present invention, a mixing ratio of the AVI-CO-004 and the nucleoside reverse transcriptase inhibitor may be adjusted in a range of 0.1 to 1:1.5 or 0.1 to 5:0.5. The AVI-CO-004 and the nucleoside reverse transcriptase inhibitor may be preferably mixed at a weight ratio of 1:3 and used.

The present invention is characterized by a synergistic effect caused by a combination of AVI-CO-004 and one or more nucleoside reverse transcriptase inhibitors. Thus, the respective active ingredients may be administered simultaneously as a composition. In addition, the respective active ingredients may be administered sequentially at time intervals during which a synergistic effect among the respective active ingredients is maintained.

The composition of the present invention may be administered orally or parenterally (for example, by intravenous, subcutaneous, intraperitoneal, or topical application) according to a desired method. In a case of oral administration, the composition may be administered as a conventional formulation such as tablets, granules, powders, capsules, pills, liquids, and syrups. In a case of parenteral administration, the composition may be administered in any formulation including injections such as intramuscular injections, suppositories, percutaneous absorption preparations, inhalation preparations, and the like.

A dosage of the composition of the present invention is administered in a therapeutically effective amount of the active ingredient, and the therapeutically effective amount means an amount sufficient to exert a sufficient HIV inhibiting effect for a specified period of time, that is, a time interval at which each formulation is taken, preferably about 24 hours. The dosage varies depending on the patient's body weight, age, sex, health condition, diet, administration time, administration method, excretion rate, severity of disease, and the like.

In a preferred embodiment of the present invention, a daily dosage of the AVI-CO-004 may be about 5 to 500 mg/kg and preferably about 50 to 300 mg/kg; and a daily dosage of the nucleoside reverse transcriptase inhibitor may be about 10 to 1,000 mg/kg and preferably about 50 to 600 mg/kg. A daily dosage of the composition obtained by mixing the AVI-CO-004 and the nucleoside reverse transcriptase inhibitor may be about 10 to 1,000 mg/kg and preferably about 20 to 500 mg/kg, in terms of decreased amount used due to a synergistic effect.

Excellent anti-HIV activity and non-infectious virus-producing action of the composition according to the present invention can be demonstrated by way of the following examples. Compared to individual active compounds, the composition exhibits an effect which is beyond an effect obtained by simply summing up effects of the individual active compounds.

A synergistic effect of the composition is always present in a case where an action of an active combination surpasses a total action of individually applied active compounds.

An expected action for a combination of two given active compounds can be calculated as follows using the Colby equation (see S. R, Colby, "Calculating Synergistic and Antagonistic Responses of Herbicide Combinations", Weeds 1967, 15, 20-22):

$$E = X + Y - \frac{X \cdot Y}{100}$$

X is a pharmacological effect of the active ingredient X, Y is a pharmacological effect of the active ingredient Y, and E is a predicted value which is a pharmacological effect predicted in a case where the ingredients X and Y (X+Y) are mixed. If an actually measured value is larger than a predicted value, it is considered to have a synergistic effect.

Advantageous Effects of Invention

The composition of the present invention exhibits a synergistic effect in terms of anti-HIV activity as compared with a case where each of compounds is used as a single drug. Thus, the pharmaceutical composition provides sufficient anti-HIV activity and exhibits decreased side effects such as toxicity even in a case where each compound is administered in a smaller amount than a single drug thereof.

In addition, even in a case where various compounds are used in combination, the composition of the present invention exhibits an excellent effect of maintaining a non-infectious virus-producing effect of AVI-CO-004 at an equivalent or higher level or increasing such a non-infectious virus-producing effect, without any phenomenon of interference or inhibition among the compounds. Thus, the composition of the present invention can effectively inhibit emergence of drug-resistant viruses.

BRIEF DESCRIPTION OF DRAWINGS

FIG. 1 illustrates results obtained by identifying antiviral activity in a case of treatment with AVI-CO-004 alone in Example 1 of the present invention: A is a result obtained by infecting cells with HIV while simultaneously performing treatment with AVI-CO-004, and observing GFP fluorescence expression with a fluorescence microscope 4 days after the infection; and B is a result obtained by collecting virus supernatant, removing cell residues, and then quantifying viral production by p24 ELISA assay.

FIG. 2 illustrates results obtained by identifying antiviral activity in a case of combined treatment with AVI-CO-004 and AZT: A is a result obtained by infecting cells with HIV while simultaneously performing treatment with AVI-CO-004 and AZT, and observing GFP fluorescence expression with a fluorescence microscope 4 days after the infection; and B is a result obtained by collecting virus supernatant, removing cell residues, and then quantifying viral production by p24 ELISA assay.

FIG. 3 illustrates results obtained by identifying antiviral activity in a case of combined treatment with AVI-CO-004 and 3TC: A is a result obtained by infecting cells with HIV while simultaneously performing treatment with AVI-CO-004 and 3TC, and observing GFP fluorescence expression with a fluorescence microscope 4 days after the infection; and B is a result obtained by collecting virus supernatant, removing cell residues, and then quantifying viral production by p24 ELISA assay.

FIG. 4 illustrates results obtained by identifying antiviral activity in a case of combined treatment with AVI-CO-004 and TFV: A is a result obtained by infecting cells with HIV while simultaneously performing treatment with AVI-CO-004 and TFV, and observing GFP fluorescence expression with a fluorescence microscope 4 days after the infection; and B is a result obtained by collecting virus supernatant, removing cell residues, and then quantifying viral production by p24 ELISA assay.

FIG. 5 illustrates results obtained by identifying antiviral activity in a case of combined treatment with AVI-CO-004 and FTC: A is a result obtained by infecting cells with HIV while simultaneously performing treatment with AVI-CO-004 and FTC, and observing GFP fluorescence expression with a fluorescence microscope 4 days after the infection; and B is a result obtained by collecting virus supernatant, removing cell residues, and then quantifying viral production by p24 ELISA assay.

FIG. 6 illustrates results obtained by identifying antiviral activity in a case of treatment with AVI-CO-004 alone in Example 2 of the present invention: A is a result obtained by infecting cells with HIV while simultaneously performing treatment with AVI-CO-004, and observing GFP fluorescence expression with a fluorescence microscope 3 days after the infection; and B is a result obtained by collecting virus supernatant, removing cell residues, and then quantifying viral production by p24 ELISA assay.

FIG. 7 illustrates results obtained by identifying antiviral activity in a case of combined treatment with AVI-CO-004, AZT, and 3TC: A is a result obtained by infecting cells with HIV while simultaneously performing treatment with AVI-CO-004, AZT, and 3TC, and observing GFP fluorescence expression with a fluorescence microscope 3 days after the infection; and B is a result obtained by collecting virus supernatant, removing cell residues, and then quantifying viral production by p24 ELISA assay.

FIG. 8 illustrates results obtained by identifying antiviral activity in a case of combined treatment with AVI-CO-004, TFV, and FTC: A is a result obtained by infecting cells with HIV while simultaneously performing treatment with AVI-CO-004, TFV, and FTC, and observing GFP fluorescence expression with a fluorescence microscope 3 days after the infection; and B is a result obtained by collecting virus supernatant, removing cell residues, and then quantifying viral production by p24 ELISA assay.

FIG. 9 illustrates results obtained by identifying a non-infectious virus-producing effect in a case of treatment with AVI-CO-004 alone in Example 3 of the present invention: A is a result obtained by reinfecting healthy MT4 cells, which have never been infected with HIV, with virus particles produced after treatment with an anti-HIV compound, and identifying infectivity of the produced viruses by observing a level of proliferation of the viruses with a fluorescence microscope after 48 hours; and B is a result obtained by performing quantitative analysis of virus-reinfected GFP-positive cells by flow cytometry using a fluorescence-activated cell sorter.

FIG. 10 illustrates results obtained by identifying a non-infectious virus-producing effect in a case of combined treatment with AVI-CO-004, AZT, and 3TC: A is a result obtained by reinfecting healthy MT4 cells, which have never been infected with HIV, with virus particles produced after treatment with an anti-HIV compound, and identifying infectivity of the produced viruses by observing a level of proliferation of the viruses with a fluorescence microscope after 48 hours; and B is a result obtained by performing quantitative analysis of virus-reinfected GFP-positive cells by flow cytometry using a fluorescence-activated cell sorter.

FIG. 11 illustrates results obtained by identifying a non-infectious virus-producing effect in a case of combined treatment with AVI-CO-004, TFV, and FTC: A is a result obtained by reinfecting healthy MT4 cells, which have never been infected with HIV, with virus particles produced after treatment with an anti-HIV compound, and identifying infectivity of the produced viruses by observing a level of proliferation of the viruses with a fluorescence microscope after 48 hours; and B is a result obtained by performing quantitative analysis of virus-reinfected GFP-positive cells by flow cytometry using a fluorescence-activated cell sorter.

FIG. 12 illustrates results obtained by identifying cytotoxicity in a case of combined treatment with AVI-CO-004, AZT, and 3TC: A is a result obtained by identifying cytotoxicity in a case of treating MT4 cells with AZT/3TC; B is a result obtained by identifying cytotoxicity in a case of treating MT4 cells with AVI-CO-004 and AZT/3TC; C is a result obtained by identifying cytotoxicity in a case of treating 293T cells with AZT/3TC; and D is a result obtained by identifying cytotoxicity in a case of treating 293T cells with AVI-CO-004 and AZT/3TC.

FIG. 13 illustrates results obtained by identifying cytotoxicity in a case of combined treatment with AVI-CO-004, TFV, and FTC: A is a result obtained by identifying cytotoxicity in a case of treating MT4 cells with TFV/FTC; B is a result obtained by identifying cytotoxicity in a case of treating MT4 cells with AVI-CO-004 and TFV/FTC; C is a result obtained by identifying cytotoxicity in a case of treating 293T cells with TFV/FTC; and D is a result obtained by identifying cytotoxicity in a case of treating 293T cells with AVI-CO-004 and TFV/FTC.

DETAILED DESCRIPTION OF INVENTION

Hereinafter, the present invention will be described in more detail by way of examples. It will be apparent to those skilled in the art that these examples are only for more specifically describing the present invention and that the scope of the present invention is not limited by these examples in accordance with the gist of the present invention.

EXAMPLES

Example 1. Identification of Synergistic HIV Inhibition Caused by Combined Treatment with AVI-CO-004 and Nucleoside Reverse Transcriptase Inhibitor 1-1. Cell Culture MT4 cells (a type of T cell line) were cultured in RPMI supplemented with 10% FBS and 10% antibiotics (penicillin and streptomycin). The cells were subcultured every 2 days in a humidified incubator at 37° C. and 5% $CO_2$ for maintenance.

1-2. Antiviral Assay

All viruses used for infection are NL43-derived HIV-1 carrying the GFP gene. The viral gene is recombined with the GFP gene, so that an expression rate of GFP may represent a level of viral infection. In order to identify antiviral efficacy, MT4 cells, which are a human-derived T cell line, were used. The MT4 cells were inoculated into 48-well plates at a density of $1 \times 10^5$ cells/well and infected with HIV-1 in an amount corresponding to 0.5 ng of HIV-1 p24. Treatment with mixtures to be tested for efficacy was performed simultaneously with the infection. The mixtures were prepared by mixing AVI-CO-004 with AZT, 3TC, Tenofovir, or FTC, respectively. Three days after the infection, GFP fluorescence expression was observed with a fluorescence microscope to identify a level of viral proliferation. Virus supernatant was collected and cell residues were removed. Then, analysis was performed. The viral production was quantified by p24 ELISA assay.

1-3. Identification of HIV Inhibition in Case of Treatment with AVI-CO-004 Alone (FIG. 1)

In order to identify synergistic HIV inhibition by combined treatment with AVI-CO-004 and a nucleoside reverse transcriptase inhibitor, antiviral efficacy in a case of treatment with AVI-CO-004 alone was first identified.

Specifically, 100,000 MT4 cells were respectively inoculated into 48-well plates and infected with HIV-1 in an amount corresponding to 0.5 ng of HIV-1 p24. Treatment with AVI-CO-004 was performed at indicated concentrations. After 4 days, an amount of viruses produced was quantified by p24 ELISA assay.

As a result, as illustrated in FIG. 1, a concentration-dependent antiviral effect of the AVI-CO-004 compound was identified (p<0.05) from the fact that in a case of treatment with AVI-CO-004 alone, an amount of viruses produced decreases as a concentration of AVI-CO-004 increases. The specific viral production may be different from the result in Example 2-1 to be described later. However, this difference is due to a difference in potency of raw materials used in Examples 1 and 2, a difference in viral activity, and the like. It will be apparent to those skilled in the art that such a difference has no influence on ascertaining a synergistic effect caused by combined use in each example.

1-4. Identification of Synergistic Effect of AVI-CO-004 with AZT in Terms of HIV Inhibitory Activity (FIG. 2)

In the present experiment, antiviral efficacy of a mixture of AVI-CO-004 and AZT was identified. First, 100,000 MT4 cells were respectively inoculated into 48-well plates and infected with HIV-1 in an amount corresponding to 0.5 ng of HIV-1 p24. Treatment with a mixture of AVI-CO-004 and AZT was performed at indicated concentrations. After 4 days, an amount of viruses produced was quantified by p24 ELISA assay.

As a result, as illustrated in FIG. 2, it was identified that a mixture of AZT and AVI-CO-004 significantly decreases viral production as compared with a case of treatment with AZT alone (p<0.05). Specifically, in a case where treatment with AZT alone is performed, an antiviral effect of 9% was exhibited; and in a case where treatment with 2.5 µM of AVI-CO-004 alone was performed according to Example 1-3, an antiviral effect of 12% was exhibited. On the other hand, in a case where AZT is mixed with 2.5 µM of AVI-CO-004, viral inhibition increased from 9% to 51% and from 12% to 51%, respectively, as compared with cases before combined treatment, and thus a very strong synergistic effect in terms of antiviral effect was exhibited (Table 1).

1-5. Identification of Synergistic Effect of AVI-CO-004 with 3TC in Terms of HIV Inhibitory Activity (FIG. 3)

In the present experiment, antiviral efficacy of a mixture of AVI-CO-004 and 3TC was identified. First, 100,000 MT4 cells were respectively inoculated into 48-well plates and infected with HIV-1 in an amount corresponding to 0.5 ng of HIV-1 p24. Treatment with a mixture of AVI-CO-004 and 3TC was performed at indicated concentrations. After 4 days, an amount of viruses produced was quantified by p24 ELISA assay.

As a result, as illustrated in FIG. 3, it was identified that a mixture of 3TC and AVI-CO-004 significantly decreases viral production as compared with a case of treatment with 3TC alone ($p<0.05$). Specifically, in a case where treatment with 3TC alone is performed, an antiviral effect of 25% was exhibited; and in a case where treatment with 2.5 µM of AVI-CO-004 alone was performed according to Example 1-3, an antiviral effect of 12% was exhibited. On the other hand, in a case where 3TC is mixed with 2.5 µM of AVI-CO-004, viral inhibition increased from 25% to 56% and from 12% to 56%, respectively, as compared with cases before combined treatment, and thus a very strong synergistic effect in terms of antiviral effect was exhibited (Table 2).

1-6. Identification of Synergistic Effect of AVI-CO-004 with TFV in Terms of HIV Inhibitory Activity (FIG. 4)

In the present experiment, antiviral efficacy of a mixture of AVI-CO-004 and TFV was identified. First, 100,000 MT4 cells were respectively inoculated into 48-well plates and infected with HIV-1 in an amount corresponding to 0.5 ng of HIV-1 p24. Treatment with a mixture of AVI-CO-004 and TFV was performed at indicated concentrations. After 4 days, an amount of viruses produced was quantified by p24 ELISA assay.

As a result, as illustrated in FIG. 4, it was identified that a mixture of TFV and AVI-CO-004 significantly decreases viral production as compared with a case of treatment with TFV alone ($p<0.05$). Specifically, in a case where treatment with TFV alone is performed, an antiviral effect of 30% was exhibited; and in a case where treatment with 2.5 µM of AVI-CO-004 alone was performed according to Example 1-3, an antiviral effect of 12% was exhibited. On the other hand, in a case where TFV is mixed with 2.5 µM of AVI-CO-004, viral inhibition increased from 30% to 50% and from 12% to 50%, respectively, as compared with cases before combined treatment, and thus a very strong synergistic effect in terms of antiviral effect was exhibited (Table 3).

1-7. Identification of Synergistic Effect of AVI-CO-004 with FTC in Terms of HIV Inhibitory Activity (FIG. 5)

In the present experiment, antiviral efficacy of a mixture of AVI-CO-004 and FTC was identified. First, 100,000 MT4 cells were respectively inoculated into 48-well plates and infected with HIV-1 in an amount corresponding to 0.5 ng of HIV-1 p24. Treatment with a mixture of AVI-CO-004 and FTC was performed at indicated concentrations. After 4 days, an amount of viruses produced was quantified by p24 ELISA assay.

As a result, as illustrated in FIG. 5, it was identified that a mixture of FTC and AVI-CO-004 significantly decreases viral production as compared with a case of treatment with FTC alone ($p<0.05$). Specifically, in a case where treatment with FTC alone is performed, an antiviral effect of 19% was exhibited; and in a case where treatment with 2.5 µM of AVI-CO-004 alone was performed according to Example 1-3, an antiviral effect of 12% was exhibited. On the other hand, in a case where FTC is mixed with 2.5 µM of AVI-CO-004, viral inhibition increased from 19% to 38% and from 12% to 38%, respectively, as compared with cases before combined treatment, and thus a very strong synergistic effect in terms of antiviral effect was exhibited (Table 4).

1-8. Identification of Synergistic Effect in Terms of HIV Inhibitory Activity Through Comparison Between Theoretical and Actually Measured Values In order to additionally verify a synergistic effect caused by combined administration based on the results obtained in the experiments for the present invention, the results obtained by comparing theoretical values calculated by the Colby equation and actually measured values are shown in the following Tables 1 to 4.

As shown in the following Table 1, in a case of combined administration of AVI-CO-004 and AZT, an actually measured virus inhibitory value is 51% which is a remarkably higher than a theoretical value of 19.92%. Thus, it is possible to identify that the combined administration exhibits synergistically enhanced activity as compared with a case of application of the active compound alone.

TABLE 1

| Test material | Amount used | Actually measured virus inhibitory value (%) | Theoretical virus inhibitory value (%) |
|---|---|---|---|
| AVI-CO-004 | 2.5 µM | 12 | |
| | 5 µM | 40 | |
| AZT | 1 nM | 9 | |
| AVI-CO-004 + | 2.5 µM + 1 nM | 51 | 19.92 |
| AZT | 5 µM + 1 nM | 59 | 45.4 |

As shown in the following Table 2, in a case of combined administration of AVI-CO-004 and 3TC, an actually measured virus inhibitory value is 56% which is a remarkably higher than a theoretical value of 34%. Thus, it is possible to identify that the combined administration exhibits synergistically enhanced activity as compared with a case of application of the active compound alone.

TABLE 2

| Test material | Amount used | Actually measured virus inhibitory value (%) | Theoretical virus inhibitory value (%) |
|---|---|---|---|
| AVI-CO-004 | 2.5 µM | 12 | |
| | 5 µM | 40 | |

TABLE 2-continued

| Test material | Amount used | Actually measured virus inhibitory value (%) | Theoretical virus inhibitory value (%) |
|---|---|---|---|
| 3TC | 1 nM | 25 | |
| AVI-CO-004 + 3TC | 2.5 µM + 1 nM | 56 | 34 |
| | 5 µM + 1 nM | 66 | 55 |

As shown in the following Table 3, in a case of combined administration of AVI-CO-004 and TFV, an actually measured virus inhibitory value is 50% which is a remarkably higher than a theoretical value of 38.4%. Thus, it is possible to identify that the combined administration exhibits synergistically enhanced activity as compared with a case of application of the active compound alone.

TABLE 3

| Test material | Amount used (µM) | Actually measured virus inhibitory value (%) | Theoretical virus inhibitory value (%) |
|---|---|---|---|
| AVI-CO-004 | 2.5 | 12 | |
| | 5 | 40 | |
| TFV | 0.25 | 30 | |
| AVI-CO-004 + TFV | 2.5 + 0.25 | 50 | 38.4 |
| | 5 + 0.25 | 66 | 58 |

As shown in the following Table 4, in a case of combined administration of AVI-CO-004 and FTC, an actually measured virus inhibitory value is 38% which is a remarkably higher than a theoretical value of 28.72%. Thus, it is possible to identify that the combined administration exhibits synergistically enhanced activity as compared with a case of application of the active compound alone.

TABLE 4

| Test material | Amount used | Actually measured virus inhibitory value (%) | Theoretical virus inhibitory value (%) |
|---|---|---|---|
| AVI-CO-004 | 2.5 µM | 12 | |
| | 5 µM | 40 | |
| FTC | 5 nM | 19 | |
| AVI-CO-004 + FTC | 2.5 µM + 5 nM | 38 | 28.72 |
| | 5 µM + 5 nM | 64 | 51.4 |

These results mean that combined administration of AVI-CO-004 and a nucleoside reverse transcriptase inhibitor (NRTI) exhibits a synergistic effect in terms of anti-HIV activity as compared with a case of using each of AVI-CO-004 or a conventional NRTI alone, and thus can further decrease an amount used of AVI-CO-004, or NRTI such as AZT, 3TC, TFV, and FTC, also suggesting that an amount used which is accompanied by side effects such as generation of resistant viruses can be decreased. Therefore, the present results ultimately suggest that AVI-CO-004 and NRTI have different therapeutic mechanisms from each other in terms of HIV inhibitory mechanism.

Example 2. Identification of HIV Inhibition Caused by AVI-CO-004 and "Mixture of Nucleoside Reverse Transcriptase Inhibitors"

2-1. Identification of HIV Inhibition in Case of Treatment with AVI-CO-004 Alone (FIG. 6)

In order to identify synergistic HIV inhibition caused by combined treatment with AVI-CO-004 and two NRTI agents, antiviral efficacy in a case of treatment with AVI-CO-004 alone was first identified.

Specifically, MT4 cells were inoculated at $1 \times 10^5$ cells into 48-well plates and infected with HIV-1 in an amount corresponding to 1 ng of p24. All viruses used for the infection are NL43-derived HIV-1 carrying the GFP gene. Together with the infection, the cells were treated with 0.5 µM, 1 µM, 2.5 µM, or 5 µM of AVI-CO-004 alone. Three days after the infection, a level of viral proliferation was identified by GFP expression using a fluorescence microscope (A of FIG. 6). Virus supernatant was collected and cell residues were removed; and HIV-1 P24 antigen ELISA assay was performed to identify a level of viral production (B of FIG. 6).

As a result, in a case of treatment with AVI-CO-004 alone, an antiviral effect was identified, on average, at 14.4% at 0.5 µM, 44% at 1 µM, 61.2% at 2.5 µM, and 76.3% at 5 µM (FIG. 6).

2-2. Identification of Synergistic Effect of AVI-CO-004 with AZT/3TC in Terms of HIV Inhibitory Activity (FIG. 7)

An examination was conducted to see whether a synergy effect is exhibited in a case where AVI-CO-004 is additionally mixed with AZT and 3TC which are two nucleoside reverse transcriptase inhibitor (NRTI)-type inhibitors. The current standard therapy for treating AIDS is based on combined use of two NRTI agents and one additional drug, and thus a baseline regimen of NRTI types was selected. AZT/3TC is a composition of Combivir preparation which is an approved AIDS therapeutic agent. Concentrations used for AZT and 3TC were selected on the basis of concentrations corresponding to ½ or ¼ of IC50 of AZT (zidovudine) identified in cell preliminary experiments, based on a formulation ratio of the actual Combivir pharmaceutical product.

First, MT4 cells were inoculated at $1 \times 10^5$ cells into 48-well plates and infected with HIV-1 in an amount corresponding to 1 ng of p24. Together with the infection, the cells were treated with AVI-CO-004 at 0.5 µM and 1 µM in combination with 1 nM of AZT (zidovudine) and 0.5 nM of 3TC (lamivudine) fixed as basal therapeutic agents. Three days after the infection, a level of viral proliferation was identified by GFP expression using a fluorescence microscope (A of FIG. 7). Virus supernatant was collected and cell residues were removed; and HIV-1 P24 antigen ELISA assay was performed to identify a level of viral production (B of FIG. 7).

As shown in Table 5 below, in a case where treatment with a mixture of AZT and 3TC (1 nM of AZT and 0.5 nM of 3TC: 1.5 nM in total) alone was performed, an antiviral effect of 34.5% was exhibited; and in a case where treatment with AVI-CO-004 alone at 0.5 µM is performed according to Example 2-1, an antiviral effect of 14.4% was exhibited.

However, in a case where a mixture of AZT and 3TC (1 nM of AZT and 0.5 nM of 3TC: 1.5 nM in total) is mixed with 0.5 µM of AVI-CO-004, viral inhibition increased from from 34.5% to 64.1% and 14.4% to 64.1%, respectively, as compared with cases before combined treatment, and thus a very strong synergistic effect in terms of antiviral effect was exhibited. In order to additionally verify a synergistic effect of the combined treatment, a theoretical value calculated by the Colby equation and an actually measured value were compared. As a result, the actually measured virus inhibitory value is 64.1% which is a remarkably higher than a theoretical value of 43.9%. Thus, it is possible to identify that the combined treatment exhibits synergistically enhanced activity as compared with a case of application of the active compound alone (Table 5). These results mean that AVI-CO-004 exhibits a synergistic effect on patients using conventional Combivir (AZT/3TC) or ordinary people, and thus can further decrease an amount used of AVI-CO-004, also suggesting that an amount used of Combivir which is accompanied by side effects such as generation of resistant viruses can be decreased. Therefore, the present results ultimately suggest that AVI-CO-004 and AZT/3TC have different therapeutic mechanisms from each other in terms of HIV inhibitory mechanism.

TABLE 5

| Test material | Amount used | Actually measured virus inhibitory value (%) | Theoretical virus inhibitory value (%) |
|---|---|---|---|
| AVI-CO-004 | 0.5 μM | 14.4 | |
| | 1 μM | 44.0 | |
| | 2.5 μM | 61.2 | |
| | 5 μM | 76.3 | |
| AZT/3TC | 1.5 nM | 34.5 | |
| AVI-CO-004 + AZT/3TC | 0.5 μM + 1.5 nM | 64.1 | 43.9 |
| | 1 μM + 1.5 nM | 67.3 | 63.32 |

2-3. Identification of Synergistic Effect of AVI-CO-004 with TFV/FTC in Terms of HIV Inhibitory Activity (FIG. 8)

An examination was conducted to see whether a synergy effect is exhibited in a case where AVI-CO-004 is additionally mixed with TFV and FTC which are two other NRTI-type inhibitors. TFV/FTC is a composition of Truvada preparation which is an approved AIDS therapeutic agent.

First, MT4 cells were inoculated at $1 \times 10^5$ cells into 48-well plates and infected with HIV-1 in an amount corresponding to 1 ng of p24. Together with the infection, the cells were treated with AVI-CO-004 at 0.5 μM, 1 μM, 2.5 μM, and 5 μM in combination with 0.25 μM of TFV and 0.2 μM of FTC fixed as basal therapeutic agents. Three days after the infection, a level of viral proliferation was identified by GFP expression using a fluorescence microscope (A of FIG. 8). Virus supernatant was collected and cell residues were removed; and HIV-1 P24 antigen ELISA assay was performed to identify a level of viral production (B of FIG. 8).

As shown in Table 6 below, in a case where treatment with a mixture of TFV and FTC (0.25 μM of TFV and 0.2 μM of FTC: 0.45 μM in total) alone was performed, an antiviral effect of 9.3% was exhibited; and in a case where treatment with 0.5 μM of AVI-CO-004 alone is performed according to Example 2-1, an antiviral effect of 14.4% was exhibited.

However, in a case where a mixture of TFV and FTC (0.25 μM of TFV and 0.2 μM of FTC: 0.45 μM in total) is mixed with 0.5 μM of AVI-CO-004, viral inhibition increased from 9.3% to 33.3% and from 14.4% to 33.3%, respectively, as compared with cases before combined treatment, and thus a very strong synergistic effect in terms of antiviral effect was exhibited. Furthermore, in a case of treatment with AVI-CO-004 alone at an increased concentration of 5 μM, excellent virus inhibitory activity of 76.3% was exhibited; however, in a case of being additionally mixed with a 0.45 μM mixture of TFV and FTC, it was found that inhibitory activity of 94.6% is exhibited, and thus an outstandingly increased synergic effect is achieved. In order to additionally verify a synergistic effect of the combined treatment, a theoretical value calculated by the Colby equation and an actually measured value were compared. As a result, it is possible to identify that the combined treatment exhibits synergistically enhanced activity at all concentrations as compared with the active compound (Table 6).

These results mean that due to a synergistic effect of the mixture of TFV and FTC, and AVI-CO-004, an amount used of AVI-CO-004 can be further decreased, also suggesting that an amount used of Truvada which is accompanied by side effects such as generation of resistant viruses can be decreased. Therefore, the present results ultimately suggest that AVI-CO-004 and TFV/FTC have different therapeutic mechanisms from each other in terms of HIV inhibitory mechanism.

TABLE 6

| Test material | Amount used (μM) | Actually measured virus inhibitory value (%) | Theoretical virus inhibitory value (%) |
|---|---|---|---|
| AVI-CO-004 | 0.5 | 14.4 | |
| | 1 | 44.0 | |
| | 2.5 | 61.2 | |
| | 5 | 76.3 | |
| TFV/FTC | 0.45 | 9.3 | |
| AVI-CO-004 + TFV/FTC | 0.5 + 0.45 | 33.3 | 22.8 |
| | 1 + 0.45 | 68.9 | 49.2 |
| | 2.5 + 0.45 | 80 | 64.8 |
| | 5 + 0.45 | 94.6 | 78.5 |

Example 3. Identification of Reinfectivity of AVI-CO-004 and "Mixture of Nucleoside Reverse Transcriptase Inhibitors"

3-1. Identification of Non-Infectious Virus-Producing Effect in Case of Treatment with AVI-CO-004 Alone (FIG. 9)

In order to identify reinfectivity of viruses produced after treatment with AVI-CO-004 alone, healthy T cells inoculated at $1 \times 10^5$ cells into 48-well plates were infected with the same amount (2.5 ng in p24) of purified viral particles produced in infection assay in Example 2. After 48 hours, a level of reinfectivity of the viral particles was identified by GFP expression using a fluorescence microscope. For quantification, GFP-positive cells re-infected with the viruses were counted using a fluorescence activated cell sorter (FACS) and indicated (A of FIG. 9), and the results were graphically represented (B of FIG. 9).

As a result, it was identified that in a case of being used to reinfect healthy cells, the viruses produced after treatment with AVI-CO-004 alone have significantly decreased reinfectivity as compared with a control (FIG. 9). This means that non-infectious viruses are produced in the course of viral proliferation due to the treatment with AVI-CO-004, so that repeated infection can be inhibited.

3-2. Identification of Non-Interference and Maintenance of Non-Infectious Virus-Producing Effect Due to AVI-CO-004 in Case of Combined Treatment with Nucleoside Reverse Transcriptase Inhibitors (FIGS. 10 and 11)

In order to compare reinfectivity of the viruses produced after treatment with AVI-CO-004 alone and after combined treatment with AVI-CO-004/AZT/3TC or AVI-CO-004/TFV/FTC, the purified viral particles produced after the combined treatment in Example 2 and a control which had not been treated with an inhibitor were quantified at the same amount (2.5 ng of p24), and used to reinfect healthy T cells.

First, healthy MT4 cells were inoculated at $1\times10^5$ cells into 48-well plates and infected with the same amount (2.5 ng in p24) of purified viral particles produced in infection assay in Example 2. After 48 hours, a level of reinfectivity of the viruses was identified by GFP expression using a fluorescence microscope. For quantification, GFP-positive cells re-infected with the viruses were counted using a fluorescence activated cell sorter (FACS) and indicated, and the results were graphically represented (FIGS. 10 and 11).

It was identified that reinfectivity of the viruses produced in a case of the treatment with AVI-CO-004 alone decreased by 35.8% at 0.5 μM, 65.3% at 1 μM, 97.5% at 2.5 μM, and 97.5% at 5 μM (Tables 7 and 8, and FIG. 9); reinfectivity of the viruses produced in a case of the combined treatment with AVI-CO-004/AZT/3TC decreased by 36.9% at 0.5 μM and 68.6% at 1 μM (Table 7 and FIG. 10); and reinfectivity of the viruses produced in a case of the combined treatment with AVI-CO-004/TFV/FTC decreased by 30.3% at 0.5 μM, 58.2% at 1 μM, 94.5% at 2.5 μM, and 99.7% at 5 μM (Table 8 and FIG. 11).

In other words, there was no large difference in reinfectivity of the viruses produced after the combined treatment as compared with the treatment with AVI-CO-004 alone. From these results, it was found that even in a case of combined treatment with AVI-CO-004/AZT/3TC and AVI-CO-004/TFV/FTC, an intrinsic non-infectious virus-producing effect of AVI-CO-004 is equally maintained without any phenomenon of interference or inhibition due to interactions among the therapeutic agents.

TABLE 7

| Test material | Amount used | Decreased reinfectivity (%) |
|---|---|---|
| AVI-CO-004 | 0.5 μM | 35.8 |
|  | 1 μM | 65.3 |
|  | 2.5 μM | 97.5 |
|  | 5 μM | 97.5 |
| AZT/3TC | 1.5 (1 + 0.5) nM | 20.7 |
| AVI-CO-004 + AZT/3TC | 0.5 μM + 1.5 nM | 36.9 |
|  | 1 μM + 1.5 nM | 68.6 |

TABLE 8

| Test material | Amount used (μM) | Decreased reinfectivity (%) |
|---|---|---|
| AVI-CO-004 | 0.5 | 35.8 |
|  | 1 | 65.3 |
|  | 2.5 | 97.5 |
|  | 5 | 97.5 |

TABLE 8-continued

| Test material | Amount used (μM) | Decreased reinfectivity (%) |
|---|---|---|
| TFV/FTC | 0.45(0.25 + 0.2) | 9.3 |
| AVI-CO-004 + TFV/FTC | 0.5 + 0.45 | 30.3 |
|  | 1 + 0.45 | 58.2 |
|  | 2.5 + 0.45 | 94.5 |
|  | 5 + 0.45 | 99.7 |

Example 4. Identification of Cytotoxicity in Case of Combined Treatment with AVI-CO-004 and Nucleoside Reverse Transcriptase Inhibitors

4-1. Cell Cytotoxicity Assay Method

Cell cytotoxicity assay was conducted based on measuring a level of ATP production in living cells. Five thousands MT4 cells or 1,000 293T cells were respectively inoculated into 96-well plates and treatment with therapeutic agents at indicated concentrations was performed. Five days after the combined treatment, an experiment was carried out according to an experimental manual of the CellTiter-Glo reagent kit (Promega). After cell lysis, ATP in a living cell reacts with the Glo reagent material to generate luminescence. Luminescence which is an indicator for living cells was measured using a luminescence microplate reader from Molecular Devices.

4-2. Identification of Cytotoxicity in Case of Combined Treatment with AVI-CO-004 and AZT/3TC (FIG. 12)

In the present experiment, an examination was conducted to see whether cytotoxicity was exhibited in a case where AVI-CO-004 is additionally mixed with AZT and 3TC.

First, 5,000 MT4 cells and 1,000 293T cells were respectively inoculated into 96-well plates and treatment with therapeutic agents at indicated concentrations was performed. Five days after the combination treatment, cell cytotoxicity assay was performed to identify a level of toxicity of the therapeutic agents.

As illustrated in FIG. 12, in a case of being treated with a mixture of AZT and 3TC without AVI-CO-004, when treated with AZT and 3TC at 0, 1, 5, 10, and 50 μM each, cytotoxicity of 23% was exhibited at 50 μM in MT4 cells (A of FIG. 12), and no toxic reaction was exhibited in 293T cells (C of FIG. 12). In a case of being treated with a mixture of AZT and 3TC while using AVI-CO-004 fixed at 5 μM, when treated with AZT and 3TC at 0, 1, 5, 10, and 50 μM, respectively, cytotoxicity of 35% was exhibited at 50 μM in MT4 cells (B of FIG. 12), and no toxic reaction was exhibited in 293T cells (D of FIG. 12). A level of cytotoxicity, which is exhibited in a case of the treatment with AZT/3TC at a high concentration of 50 μM, increased by 12% in a case of combined treatment with AVI-CO-004 at 5 μM, which is not a statistically significant increase. It was found that no cytotoxicity is exhibited in the concentration range (AZT, 1 nM; 3TC, 0.5 nM; AVI-CO-004, 0.5 to 1 μM), within which efficacy tests were conducted, in a case of the combined treatment with AZT/3TC/AVI-CO-004.

4-3. Identification of Cytotoxicity in Case of Combined Treatment with AVI-CO-004 and TFV/FTC (FIG. 13)

In the present experiment, an examination was conducted to see whether cytotoxicity was exhibited in a case where AVI-CO-004 is additionally mixed with TFV and FTC.

First, 5,000 MT4 cells and 1,000 293T cells were respectively inoculated into 96-well plates and treatment with therapeutic agents at indicated concentrations was performed. Five days after the combination treatment, cell viability assay was performed to identify a level of toxicity of the therapeutic agents.

As illustrated in FIG. 13, in a case of being treated with a mixture of TFV and FTC at 0, 1, 5, 10, and 50 µM each without AVI-CO-004, when treated with TFV and FTC at 50 µM each, cytotoxicity of 17% was exhibited in MT4 cells (A of FIG. 13), and no toxic reaction was exhibited in 293 T cells (C of FIG. 13). In a case of being treated with a mixture of TFV and FTC at 0, 1, 5, 10, and 50 µM each while using AVI-CO-004 fixed at 5 µM, when treated with AVI-CO-004 at 5 µM, and TFV and FTC at 50 µM each, cytotoxicity of 26% was exhibited at 50 µM in MT4 cells (B of FIG. 13), and no toxic reaction was exhibited in 293 T cells (D of FIG. 13). A level of cytotoxicity, which is exhibited in a case of the treatment with TFV/FTC at a high concentration of 50 µM, increased by 9% in a case of combined treatment with AVI-CO-004 at 5 µM, which is not a statistically significant increase. It was found that no cytotoxicity is exhibited in the concentration range (TFV, 0.25 µM; FTC, 0.2 µM; AVI-CO-004, 0.5 to 5 µM), within which efficacy tests were conducted, in a case of the combined treatment with TFV/FTC/AVI-CO-004.

As stated above, specific portions of the present invention have been described in detail. However, it will be apparent to those skilled in the art that such specific description is merely intended to represent preferred embodiments and that the scope of the present invention is not limited thereto. Accordingly, the actual scope of the present invention will be defined by the appended claims and equivalents thereof.

What is claimed is:

1. A method of preventing or treating AIDS, comprising:
administering, to a subject in need of such prevention or treatment, a nucleoside reverse transcriptase inhibitor (NRTI) and a compound of Formula 1 or a pharmaceutically acceptable salt thereof:

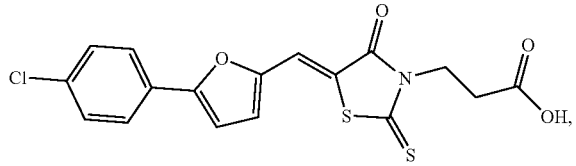 [SMILES: O=C(O)CCN1C(=O)/C(=C/c2ccc(-c3ccc(Cl)cc3)o2)SC1=S]

wherein the NRTI is one or more selected from the group consisting of emtricitabine (FTC), lamivudine (3TC), tenofovir (TFV), a pharmaceutically acceptable salt of any of these, and a prodrug of the tenofovir (TFV), wherein the compound of Formula 1 is in an amount of about 2.5 µM, the emtricitabine (FTC) is in an amount of about 5 nM, the lamivudine (3TC) is in an amount of about 1 nM, the tenofovir (TFV) is in an amount of about 0.25 µM, and the prodrug of the tenofovir (TFV) is in an amount which is metabolized into about 0.25 µM of the tenofovir (TFV) after administration, and wherein said combination of the NRTI and the compound of Formula 1 yields a greater than additive or synergistic effect as compared to an actually measured virus inhibitory value of each agent alone.

2. The method according to claim 1, wherein the NRTI or the pharmaceutically acceptable salt or prodrug thereof and the compound of Formula (1) or the pharmaceutically acceptable salt thereof are administered simultaneously or sequentially.

3. The method according to claim 1, wherein the NRTI or the pharmaceutically acceptable salt or prodrug thereof and the compound of Formula (1) or the pharmaceutically acceptable salt thereof are administered together in the form of a composition comprising the NRTI or the pharmaceutically acceptable salt or prodrug thereof and the compound of Formula (1) or the pharmaceutically acceptable salt thereof.

* * * * *